United States Patent
Hussein et al.

(10) Patent No.: US 10,178,464 B2
(45) Date of Patent: Jan. 8, 2019

(54) EARPIECE

(71) Applicant: Racal Acoustics Ltd., Harrow (GB)

(72) Inventors: Habib Hussein, Harrow (GB); Norman Davidson, Harrow (GB)

(73) Assignee: Racal Acoustics Limited, Harrow Middlesex (GB)

( * ) Notice: Subject to any disclaimer, the term of this patent is extended or adjusted under 35 U.S.C. 154(b) by 0 days.

(21) Appl. No.: 15/030,369

(22) PCT Filed: Oct. 23, 2014

(86) PCT No.: PCT/GB2014/053156
§ 371 (c)(1),
(2) Date: Apr. 18, 2016

(87) PCT Pub. No.: WO2015/059474
PCT Pub. Date: Apr. 30, 2015

(65) Prior Publication Data
US 2016/0286300 A1    Sep. 29, 2016

(30) Foreign Application Priority Data
Oct. 23, 2013   (GB) .................................. 1318717.4

(51) Int. Cl.
| | |
|---|---|
| *H04R 1/10* | (2006.01) |
| *A61F 11/08* | (2006.01) |
| *H04R 1/34* | (2006.01) |
| *A61F 11/14* | (2006.01) |

(52) U.S. Cl.
CPC ............ *H04R 1/1075* (2013.01); *A61F 11/08* (2013.01); *H04R 1/105* (2013.01); *H04R 1/1016* (2013.01); *H04R 1/1083* (2013.01); *H04R 1/342* (2013.01); *A61F 2011/145* (2013.01); *H04R 2410/07* (2013.01)

(58) Field of Classification Search
CPC .................. H04R 25/65; H04R 25/652; H04R 2225/025; H04R 25/40; H04R 1/1066
USPC ................ 381/322, 359, 356, 357, 313, 328
See application file for complete search history.

(56) References Cited

U.S. PATENT DOCUMENTS

| | | | | |
|---|---|---|---|---|
| 9,426,558 | B2 * | 8/2016 | Burt ..................... | H04R 1/1066 |
| 2006/0078141 | A1 * | 4/2006 | Jessen .................. | H04R 25/402 |
| | | | | 381/313 |
| 2013/0216060 | A1 * | 8/2013 | Narayan ................ | H04R 3/005 |
| | | | | 381/71.6 |
| 2014/0205131 | A1 * | 7/2014 | Azmi .................... | H04R 1/1075 |
| | | | | 381/380 |
| 2015/0110320 | A1 * | 4/2015 | Liu ....................... | H04R 1/1016 |
| | | | | 381/322 |

* cited by examiner

*Primary Examiner* — Alexander Jamal
(74) *Attorney, Agent, or Firm* — Perkins Coie LLP

(57) ABSTRACT

An earpiece comprising an earbud, which is arranged such that it may be inserted into the ear canal of a user, and a housing, which houses at least one microphone that is arranged to sample the ambient environment, the housing comprising a port through which sound may be received by the microphone, the earpiece being arranged such that when the earbud is inserted into the ear canal of a user the microphone samples the ambient environment between the earpiece and the concha.

17 Claims, 6 Drawing Sheets

EARPIECE

CROSS REFERENCE TO RELATED APPLICATIONS

The present application is a 35 U.S.C. § 371 U.S. National Phase application of International Patent Application No. PCT/GB2014/053156, filed Oct. 23, 2014, which claims priority to Great Britain Patent Application No. 1318717.4, filed Oct. 23, 2013, both of which are incorporated herein by reference in their entireties.

TECHNICAL FIELD

The present disclosure relates to an earpiece suitable for a hearing protection device, which hearing protection device is suitable for providing hearing protection in environments with medium or high ambient noise whilst providing a situational awareness and/or communications capability.

BACKGROUND

People performing tasks in an environment where a medium to high level of ambient noise can be encountered are required to have some form of hearing protection. Normally, a circum-aural or in-the-ear hearing protection device is employed.

When using a hearing protection device, situational awareness is reduced. Situational awareness can be restored by adding a "talk-through" function to the hearing protection device. The talk-through function allows the user of the hearing protection device to hear sounds external to the device, without having to remove the device. The typical method of adding the talk-through function is to add a microphone that samples the ambient environment. The signal from the microphone is passed to a talk-through circuit, which passes an electrical signal to a speaker and thus onto the user's hearing.

Any device that uses one or more microphones to sample the ambient environment is susceptible to noise being introduced into the microphone(s) as a result of wind. Wind acts upon a microphone in a similar way as sound pressure waves and is therefore hard to distinguish from sounds. Numerous technical and white papers detail how wind affects microphones. Particular examples are convention papers 5718, 6624, 6635 and 6879 published by Audio Engineering Society.

The greater the wind speed the greater the amount of wind noise induced into a microphone, until the wind speed reaches a level where sounds picked up by the microphone are distorted beyond recognition. The greater the speed of the wind the wider the frequency band of wind noise induced into a microphone.

Wind, by its nature, exists in a non-predictable chaotic state and can induce noise in a microphone across a broad spectrum of audio frequencies. When wind encounters obstacles, turbulence is introduced into the wind flow. The turbulence can act in a similar manner to sound and can therefore be interpreted by a device using a microphone as sound. Turbulence exacerbates the problem of wind noise.

For the purposes of simplifying the explanation of turbulence (in the context of wind hitting a person's head), an example situation is considered in which wind is blowing directly into the face of the person, which wind is homogenous and turbulence free prior to encountering the person.

With reference to FIGS. 1a, 1b and 1c, a partial horizontal cross section of the person's head (with no hearing protection device present) is used as a basis for the explanation. This is not to be viewed as an accurate representation of the person's head, it is used to illustrate principles only. The cheek (101), tragus (102), ear canal (103), ear drum (104), concha (105), the rear face of the concha (106) and the helix (107) are used as reference points.

As shown in FIG. 1a, when wind hits the cheek (101), (or similar part of the head), turbulence (202) is created within the wind. The turbulence (202) created has a length that can causes a microphone to interpret it as a low frequency audio sound.

As shown in FIGS. 1b, when wind hits the helix (107), turbulence (302) is created within the wind, which turbulence can be interpreted by a microphone as a medium frequency audio sound.

Finally, as shown in FIG. 1c, when wind hits the tragus (102), turbulence (402) is created within the wind, which turbulence can be interpreted by a microphone as a high frequency audio sound.

Research carried out by the National Acoustics Laboratory of Australia determined the wind turbulence around the ear for different wind directions and the resultant frequencies induced into a microphone. In accordance with the research, all of the turbulences within the wind created by a head, including those example turbulences in FIGS. 1a, 1b and 1c, which are shown for the purposes of explanation only, are eventually damped to zero, but the turbulences cover sufficient distance to affect any microphone near the ear.

The reduction of wind noise in microphones is a primary goal of all devices where wind can be encountered, however, to date, no suitable solution has been provided for reducing wind noise to an acceptably low level when one or more microphones are provided in an earpiece, which may be used for an in-the-ear hearing protection device or otherwise.

A prior art earpiece provided with a microphone for picking up ambient sounds is known from US 2010/0166204. Whilst this document purports to position a microphone pick-up opening so that it is not affected by wind noise, the arrangement is not effective in reducing wind noise since the microphone pick-up opening is provided on an outer face of the earpiece such that the microphone directly samples the ambient environment outside the concha.

SUMMARY

The present invention arose in a bid to provide a solution for reducing wind noise to an acceptably low level in an earpiece. The present inventors, through extensive research and experimentation, established that the effects of wind noise on a microphone provided in an in the ear earpiece could be mitigated by suitable positioning of a microphone port on the housing of the earpiece so that the microphone samples the ambient environment between the earpiece and the concha.

According to the present invention in a first aspect, there is provided an earpiece comprising an earbud, which is arranged such that it may be inserted into the ear canal of a user, and a housing, which houses at least one microphone that is arranged to sample the ambient environment, the housing comprising a port through which sound may be received by the microphone, the earpiece being arranged such that when the earbud is inserted into the ear canal of a user the microphone samples the ambient environment between the earpiece and the concha.

Preferably, the only sound received by the microphone is sound that is received through the port. Preferably, the earpiece is arranged such that the port lies within the concha. Most preferably, the port lies adjacent the rear face of the concha. The housing may be provided with one or more elements that are arranged to maintain an air gap between the port and a surface of the concha.

The port may face a surface of the pinna. In particular, the port may face the rear face of the concha.

The pinna is the visible part of the ear that resides outside of the head. The concha is the bowl-shaped part of the pinna nearest the ear canal.

The arrangement is preferably such that there is no unimpeded straight line path into the port from outside the concha.

The axis of the port may be arranged at an angle of 45 degrees or more relative to a transverse axis of the housing. Here the angle is an interior angle between the axes (as shown in FIG. 7—see angles α and β).

Further, preferred, features are presented in the dependent claims.

According to the present invention in a further aspect, there is provided a hearing protection device comprising one or more earpieces as defined above. The hearing protection device preferably comprises a pair of the earpieces.

A non-limiting embodiment will now be described, by way of example only, with reference to the accompanying drawings, in which:

DETAILED DESCRIPTION

Figure 1A:
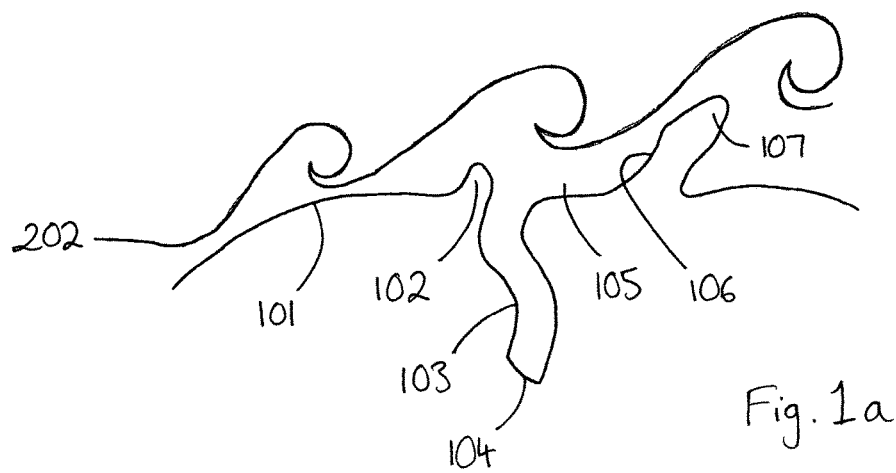
FIGS. 1a, 1b and 1c show a partial sectional view of a user's head and turbulence created by wind hitting the user's head, as described above.
Figure 1B:
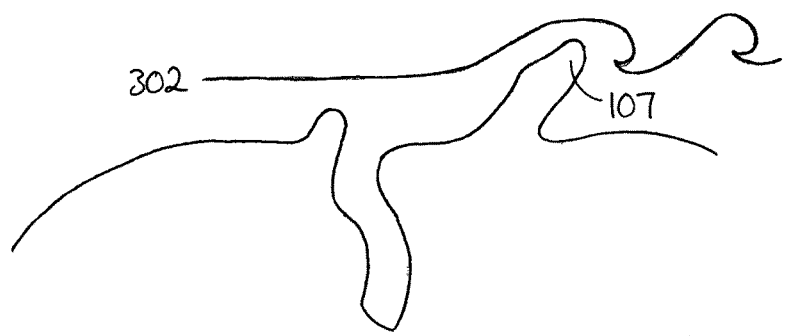
Figure 1C:
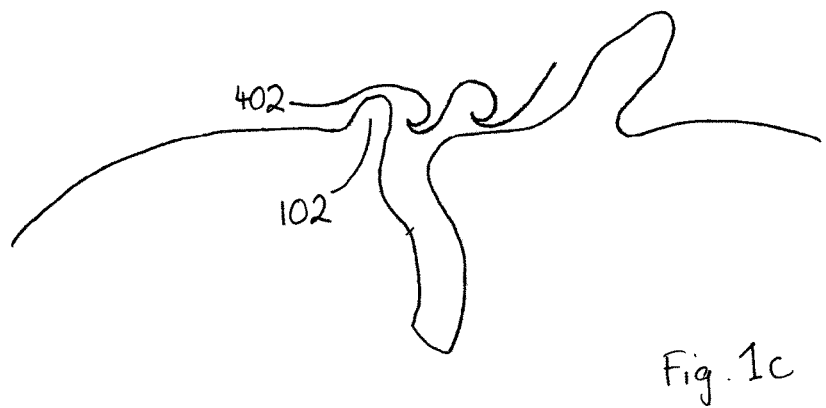
Figure 2:
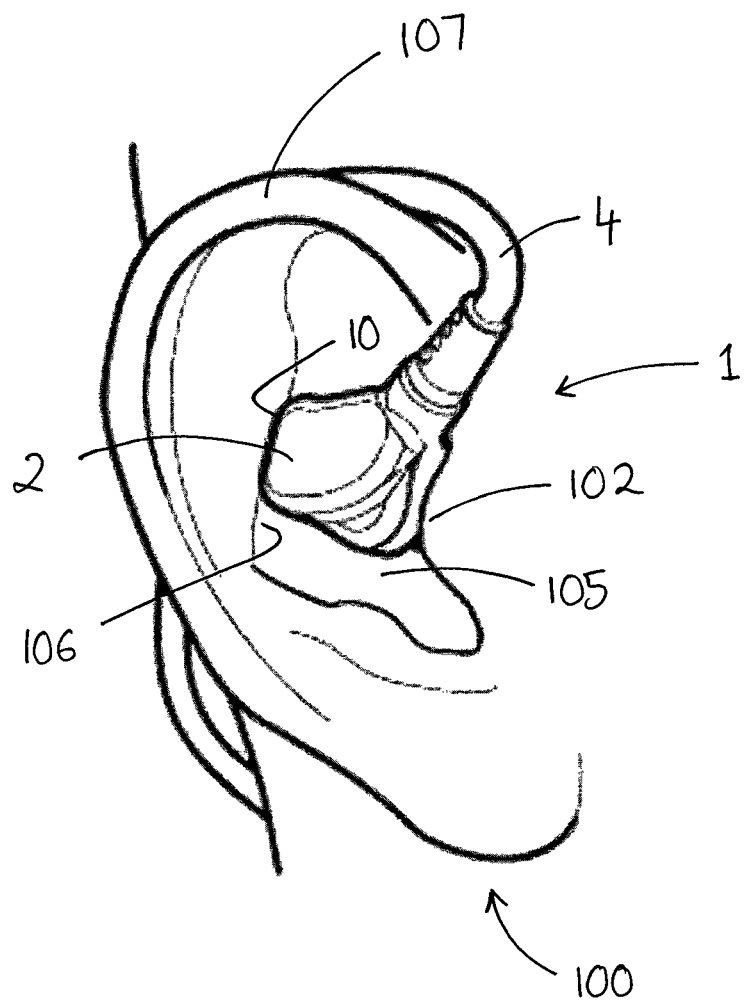
FIG. 2 is a perspective view of an earpiece in accordance with the present invention in the right ear of a user.
Figure 3:
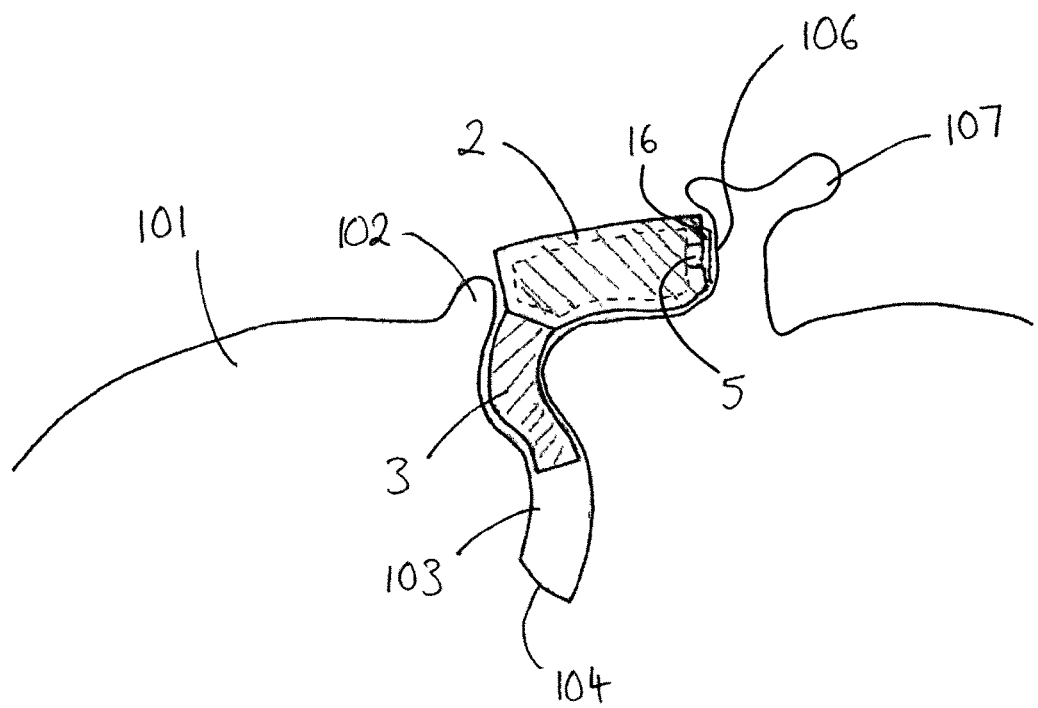
FIG. 3 shows, schematically, a partial sectional view of the user's head and earpiece shown in FIG. 2.

With reference to FIGS. 2 and 3, there is shown an earpiece (1), in accordance with a first embodiment, in use. The earpiece comprises a housing (2) and an earbud (3), which are received by the user's pinna (100). The earbud is received by the ear canal (103) and at least a portion of the housing is received by the concha (105). Within the housing, along with a number of other electrical components, as described below, is a microphone (not shown). The housing comprises a port (5) (seen most clearly in the perspective view of the housing shown in FIG. 4). Sound is received by the microphone through the port. The microphone may be mounted to an inner face of the housing behind the port. It may be mounted via a seal or gasket, which may comprise rubber or similar. Numerous suitable mounting means for the microphone within the housing will be readily appreciated by those skilled in the art.

In use, as shown schematically in FIG. 3, the port (5) is shielded from the wind by the user's pinna. Note that the port is obscured from view in FIG. 2. The port lies within the concha. By virtue of the positioning of the port, the microphone samples the ambient environment between the earpiece and the concha. The port lies adjacent to and faces the rear face (106) of the concha. In the present arrangement, in use, there is no unimpeded straight line path into the port from outside the concha. Portions of the pinna block any such path. One or more elements (such as protrusions 15, 16, 17 of FIG. 4, described below) may be provided to maintain an air gap between the port and the surface (rear face) of the concha.

In the present arrangement, as described herein, the port faces a surface of the user's pinna (100), specifically, the rear face (106) of the concha (105), as shown. It should be appreciated that alternative arrangements will be possible, however, where the port does not face a surface of the pinna, as long as the port is located so that the microphone samples the ambient environment between the earpiece and the concha. Also, there may be arrangements in which there is an unimpeded straight line path into the port from outside the concha, again as long as the port is located so that the microphone samples the ambient environment between the earpiece and the concha.

With the port located as described when the earpiece is in use, the wind noise picked up by the microphone is effectively reduced, whilst the microphone is able to pick up all desired sounds.

A cable (4) is connected to the housing. The cable carries electrical signals to/from the earpiece. Note that the cable is omitted from FIG. 3 for simplicity. Whilst the cable is shown to extend up and back over the top of the user's pinna, in alternative arrangements the connection of the cable to the housing may be such that the cable extends at an alternative angle or in a different direction, such as down. Various cable arrangements will be appreciated by those skilled in the art.

FIGS. 4 to 7 show the housing (2) of the earpiece (1) of FIG. 2 in detail. The housing may be formed, for example, from moulded plastic. The housing comprises a first (inner) face (6) and a second (outer) face (7), which is opposed to the first face.

The earbud (3, FIGS. 3 and 7) is connected to the first face. In the present arrangement a spigot (8) is provided, which extends from the first face and is arranged to engage the earbud. The spigot is preferably arranged to engage a hole in the earbud, which extends along the longitudinal axis of the earbud. The earbud may be attached to the spigot by interference fit or otherwise. It should be noted that in alternative arrangements the spigot may be omitted with an alternative means of attaching the housing and the earbud to one another being provided instead. Regardless of the attachment means, the first face is arranged to face inwardly in use (relative to a user's head) with the earbud extending therefrom for receipt by the ear canal of the user. The first face thus faces the bottom (radially outwardly facing) surface of the concha in use. To provide a comfortable fit, the first surface is preferably curved. The earbud preferably extends from the first face at an oblique angle, as shown.

The second face (7) is opposed to the first face and faces radially outwardly in use, as seen in FIG. 2. A sidewall (9) is arranged between the first and second faces. The sidewall extends between the first and second faces.

The sidewall may be considered to form first and second end faces (10, 11), which are opposed to one another, and a pair of side faces (12, 13), which extend between the end faces and are opposed to one another. In use, as seen in FIGS. 2 and 3, the first end face (10) faces the rear face (106)

of the concha (105) and the second end face (11) faces the tragus (102). The port (5) is provided in the first end face.

Figure 4:
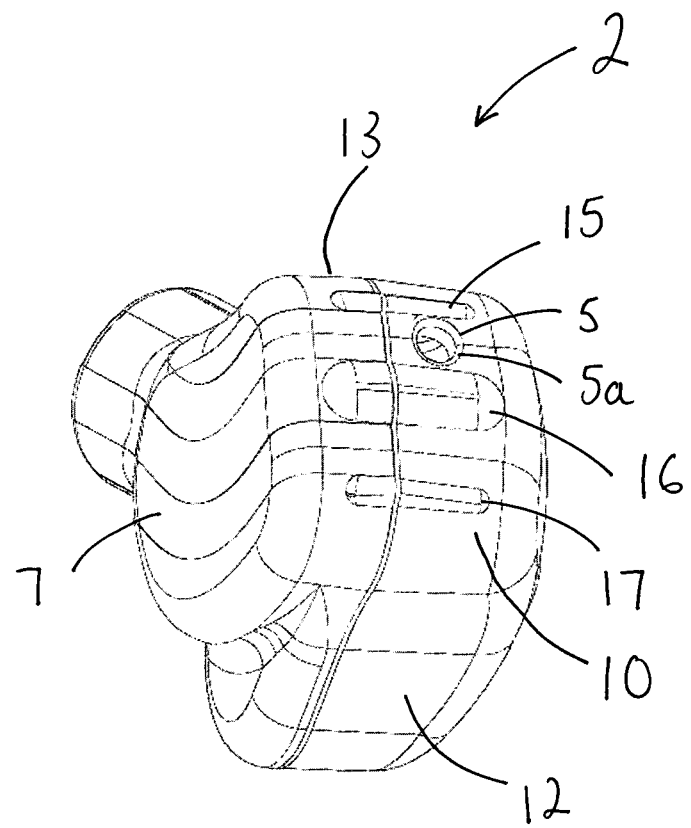
FIG. 4 is a perspective view of an earpiece housing (left) in accordance with the present invention.
Figure 5:
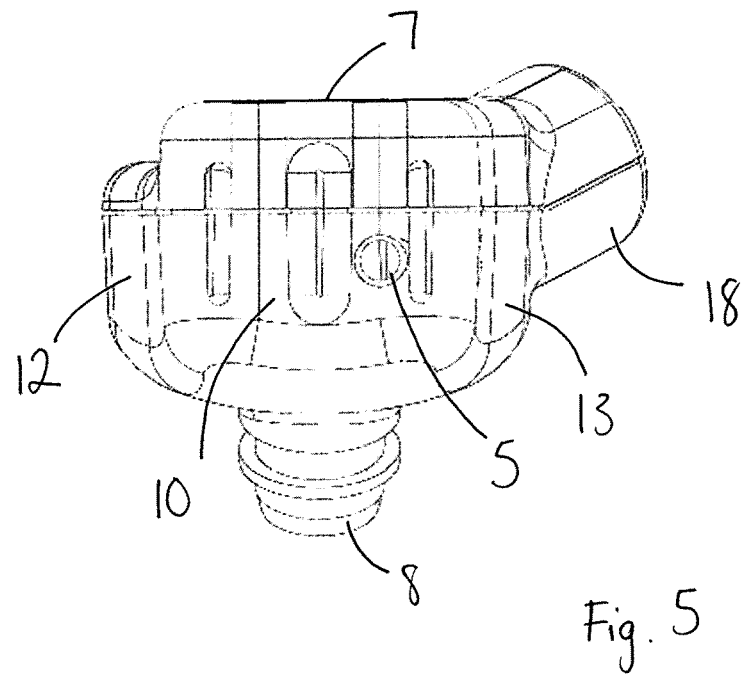
FIG. 5 shows an end view of the earpiece housing of FIG. 4.
Figure 6:
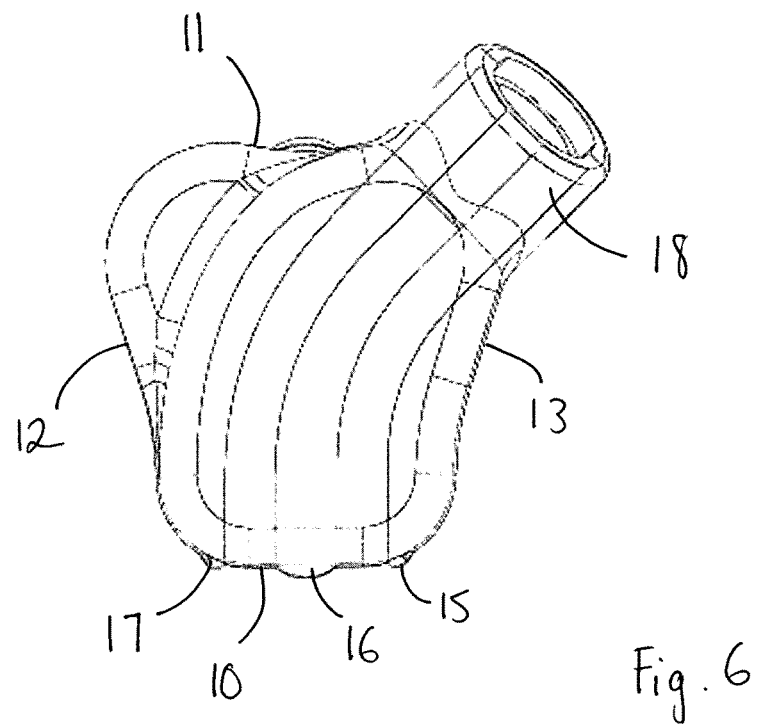
FIG. 6 shows a front view of the earpiece housing of FIG. 4.

The port comprises a hole. The hole extends through the wall of the housing. Whilst the port is shown to comprise a single circular hole in alternative arrangements, the hole may be shaped differently and/or the port may comprise a plurality of holes, which may be provided in a cluster or otherwise. The (or each) hole forming the port preferably has a radiused edge (5a), as shown in FIG. 4, most preferably the radius comprises an elliptical radius.

The first end face that is provided with the port preferably features one or more protrusions (15, 16, 17), which are located adjacent the port, as shown. The protrusions may be integrally formed with the housing. Whilst three protrusions are shown there may be more or less protrusions provided. There is preferably a protrusion provided either side of the port, most preferably the protrusions provided either side of the port are provided immediately adjacent opposed sides of the port. In the present arrangement the protrusions comprise ribs/ridges. It is preferable, as shown, that the ribs/ridges have a greater length than the diameter of the hole forming the port. The ribs/ridges protrude outwardly from the surface in the axial direction of the hole forming the port.

The protrusions are provided, in accordance with the discussion above, so that an air gap is maintained between the port and the surface (rear face) of the concha, wherein the microphone samples the ambient environment in this air gap, through the port which opens into this air gap. As will be readily appreciated by those skilled in the art, numerous alternative arrangements other than the protrusions shown may be implemented to achieve the desired result.

Whilst a particular form of housing has been described, it will be readily appreciated that alternatively shaped housings are possible.

A collar (18) is preferably provided, as shown, which collar receives and supports the wire (4). The collar may support a cable entry. The location and orientation of the collar may be varied in accordance with the desired path of the wire.

Figure 7:
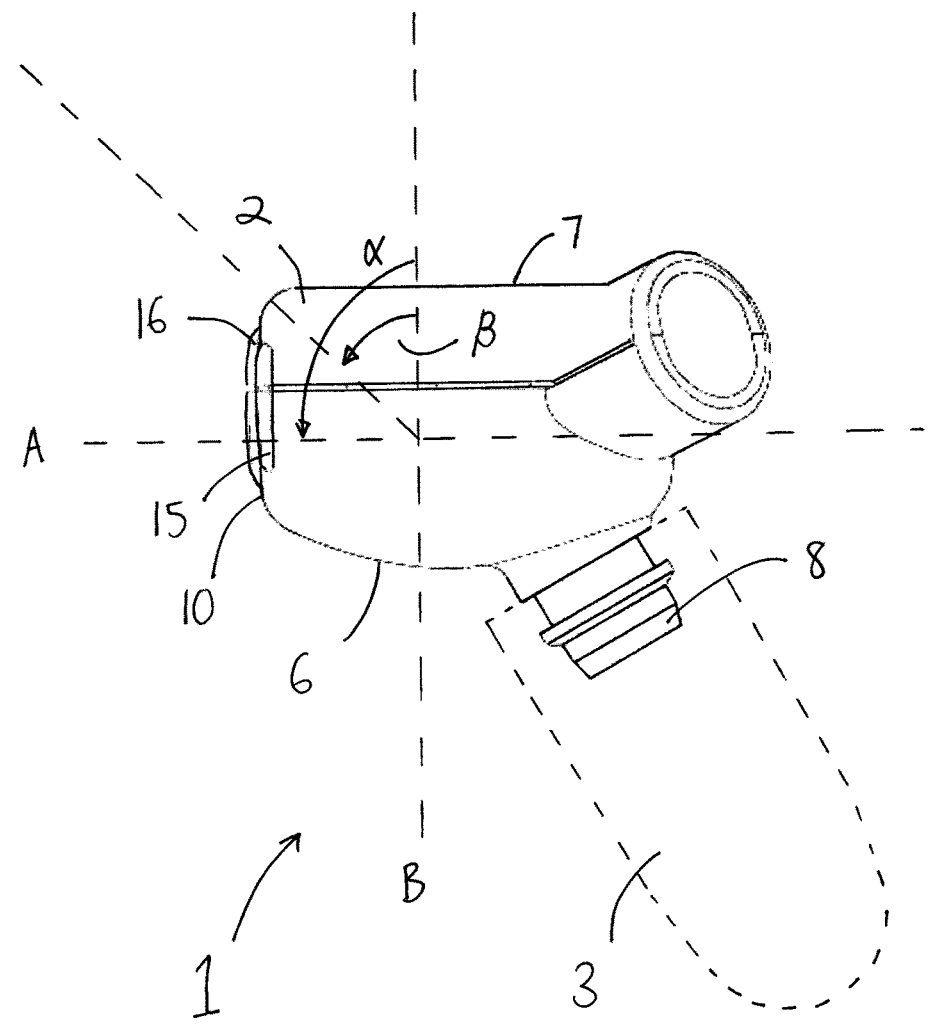
FIG. 7 shows a side (top) view of the earpiece housing of FIG. 4.

With reference to FIG. 7, the relative orientations of the port and a transverse axis B of the housing of the earpiece are considered. Note that, in use, the transverse axis B of the housing will extend radially outwardly from the head of the user.

The port, as detailed, comprises at least one hole extending through a wall of the housing, which through hole has an axis (not labeled). The housing has a longitudinal axis A and the transverse axis B, as shown. In the arrangement of FIG. 7, the through hole lies on the longitudinal axis A. In the arrangement of FIG. 7, the axis of the through hole forming the port thus lies at an angle α of 90 degrees relative to the transverse axis B. The axis of the (or each) through hole that forms the port is preferably provided at an angle of 45 degrees or more relative to the transverse axis B. For illustration purposes an angle of 45 degrees is shown as angle β in FIG. 7. The angles referred to here are interior angles between the two axes, as shown.

The earpiece is preferably configured for use in a hearing protection device, which protects the user against hearing damage in environments with medium or high ambient noise level.

A medium ambient noise environment is an environment where hearing damage or noise induced hearing loss can occur with long term exposure to the noise. The law of many countries attributes a continuous sound level of 85 dbA to this environment. Hearing damage or noise induced hearing loss can occur after an expose period of 8 hour per day in such an environment. For impulse or impact noise the level is set at 140 db peak sound pressure level (SPL).

A high ambient noise environment is an environment where hearing damage or noise induced hearing loss can occur with short term exposure to the noise. The law of many countries attributes a continuous sound level of 105 dbSPL to this environment. Hearing damage or noise induced hearing loss can occur after an expose period of 1 hour per day.

The above definitions of medium and high ambient noise environments are adopted herein.

The earbud (3) may be formed from any material commonly used for the production of typical prior art passive sound attenuating earbuds, such as silicon or foam. The earbud may be formed into a range of standard shapes and sizes or may be custom moulded. In FIG. 3, it may be seen that the earbud, formed of a pliable material, has conformed to the shape of the user's ear canal and blocks the user's ear canal.

Conventional noise reduction components/circuitry may be introduced into the earpiece, as will be readily appreciated by those skilled in the art. Such components/circuitry may comprise a feed forward circuit and a speaker in addition to the microphone. The signal of the noise appearing at the user's ear which is detected by the microphone is inverted and added to the drive signal of the speaker, creating a cancellation signal.

A "talk-through" function may be provided by the introduction of a talk-through circuit into the earpiece, which talk-through circuit passes an electrical signal from the microphone on to a speaker and thus onto the user's hearing.

The noise cancelling and talk through functions may be provided in combination with one another or independently of one another.

Various other electrical circuitry and transducers may be introduced into any earpiece provided with a microphone and microphone port as described above, as will be readily appreciated by those skilled in the art.

Numerous alternatives and modifications within the scope of the appended claims are possible, as will be readily appreciated by those skilled in the art.

The invention claimed is:

1. A hearing protection device comprising an earpiece, the earpiece comprising an earbud configured for insertion into the ear canal of a user, and a housing that houses at least one microphone arranged to sample the ambient environment, the housing comprising opposing first and second faces, wherein the first face faces and extends along a bottom surface of the concha when the earbud is in the ear canal and the second face faces away from the bottom surface of the concha and out of the concha, and the housing having spaced apart opposing third and fourth faces extending between the first and second faces, wherein the housing is configured with the third face being adjacent to the tragus of a user's ear and the fourth face being adjacent to the rear surface of the concha of the user's ear when the earbud is in the ear canal, wherein the housing has a longitudinal axis extending through the third and fourth faces and a transverse axis normal to the longitudinal axis and extending through the first and second faces, and a port in the fourth face of the housing and through which sound may be received by the microphone, the earbud being connected to the first face to extend outwards from the first face in an axial direction of the earbud and arranged such that when the earbud is inserted into the ear canal the microphone samples the ambient environment between the housing and a face of the concha spaced apart from the ear canal, and the fourth face has one or more protrusions adjacent the port that extend outwards in an axial direction of the port toward a rear surface of the concha spaced apart from the ear canal, wherein the protrusions are configured to maintain a gap between the port and the rear surface of the concha when the earbud is in the ear canal, and wherein the port is positioned such that there is no unimpeded straight line path into the port from outside the concha.

2. An earpiece as claimed in claim 1, wherein in the housing comprises a spigot connected to the first face of the housing, and the ear bud is connected to the spigot.

3. An earpiece as claimed in claim 2, wherein the earbud is attached to the spigot with an interference fit.

4. An earpiece as claimed in claim 1, wherein the first and fourth faces of the housing are fully exterior of the ear canal when the earbud is in the ear canal.

5. An earpiece comprising an earbud insertable into the ear canal of a user, and a housing configured to be substantially external of the ear canal when the earbud is in the ear canal, the housing containing at least one microphone arranged to sample the ambient environment, the housing comprising a port through which sound may be received by the microphone, and the housing comprising opposing first and second faces, wherein the first face faces and extends along a bottom of the concha when the earbud is in the ear canal and the second face faces away from the bottom surface of the concha and out of the concha, and the housing having spaced apart, opposing third and fourth faces extending between the first and second faces, wherein the housing is configured with the third face being adjacent to the tragus of a user's ear and the fourth face being adjacent to the rear surface of the concha of the user'ear when the earbud is in the ear canal, wherein the housing has a longitudinal axis extending through the third and fourth faces and a transverse axis normal to the longitudinal axis and extending through the first and second faces, the earpiece being arranged such that when the earbud is inserted into the ear canal of a user the microphone samples the ambient environment between the earpiece and the concha, wherein the fourth surface of the housing in which the port is provided has one or more protrusions adjacent the port and projecting toward the rear surface of the concha spaced apart from the ear canal, wherein the protrusions are configured to maintain a gap between the port and the rear surface of the concha when the earbud is in the ear canal, wherein the port is positioned closely adjacent to the rear surface of the concha such that there is no unimpeded straight line path into the port from outside the concha when the earbud is in the ear canal.

6. A hearing protection device as claimed in claim 1, wherein the earpiece is arranged such that the port lies within the concha.

7. A hearing protection device as claimed in claim 1, wherein the earpiece is arranged such that the one or more protrusions are immediately adjacent the rear surface of the concha.

8. A hearing protection device as claimed in claim 1, wherein the port faces a surface of the pinna.

9. A hearing protection device as claimed in claim 1, wherein the first face of the housing is configured to extend laterally along the bottom surface of the concha away from the earbud, and the fourth face is connected to the first face at a location spaced laterally from the earbud and adjacent to the bottom and rear surfaces of the concha.

10. A hearing protection device as claimed in claim 1 wherein the fourth face is spaced laterally apart from the earbud and configured to be immediately adjacent to the rear face of the concha.

11. A hearing protection device as claimed in claim 1, wherein the axis of the port is arranged at an angle of at least 45 degrees relative to the transverse axis of the housing.

12. A hearing protection device as claimed in claim 1, wherein the fourth face formed by a sidewall substantially perpendicular to the first face.

13. A hearing protection device as claimed in claim 1, wherein the protrusions comprise a pair of protrusions with one protrusion provided on either side of the port.

14. A hearing protection device as claimed in claim 1 wherein the one or more protrusions comprise a rib or ridge having a length greater than the port.

15. A hearing protection device as claimed in claim 1, wherein the port comprises one or more holes extending through a wall of the housing.

16. A hearing protection device as claimed in claim 1, wherein the port comprises at least one hole extending through the wall of the housing, and the at least one hole comprises a radiused edge.

17. A hearing protection device comprising an earpiece comprising an earbud, which is arranged such that it may be inserted into the ear canal of a user, and a housing, which houses at least one microphone that is arranged to sample the ambient environment, the housing comprising opposing first and second end faces and opposing first and second side faces extending between the first and second end faces, the housing is configured with the first end face spaced laterally apart from the ear canal and being immediately adjacent to the rear face of the concha, and the second end faces the tragus of the ear, the first side face configured to extend laterally away from the ear canal adjacent to the bottom surface of the concha and connect to the first end face adjacent to the bottom and rear surfaces of the concha, the earbud projecting axially away from the first side face and configured to extend into the ear canal, the housing having a port in the first end wall through which sound may be received by the microphone, wherein the first end face of the housing having one or more protrusions adjacent the port that extend outwards in an axial direction of the port and configured to space the port away from the rear surface of the concha, the one or more protrusions being spaced laterally away from the ear canal and being configured to engage the rear surface of the concha to block the rear surface of the concha from covering the port, the housing being arranged such that when the earbud is in the ear canal of the user, the microphone samples the ambient environment between the earpiece and the concha, wherein the port is positioned closely adjacent to the rear surface of the concha such that there is no unimpeded straight line path into the port from outside the concha when the earbud is in the ear canal.

* * * * *